(12) United States Patent
Nakatomi et al.

(10) Patent No.: US 10,925,304 B2
(45) Date of Patent: Feb. 23, 2021

(54) METHOD FOR TREATING CHRONIC FATIGUE SYNDROME, IDIOPATHIC CHRONIC FATIGUE, AND FIBROMYALGIA

(71) Applicant: PRODUCTIVE AGING LABORATORY, CO., LTD., Osaka (JP)

(72) Inventors: Yasuhito Nakatomi, Hyogo (JP); Yosky Kataoka, Hyogo (JP); Yo-ichi Nabeshima, Kyoto (JP)

(73) Assignee: PRODUCTIVE AGING LABORATORY, CO., LTD., Osaka (JP)

( * ) Notice: Subject to any disclaimer, the term of this patent is extended or adjusted under 35 U.S.C. 154(b) by 0 days.

(21) Appl. No.: 16/474,637

(22) PCT Filed: Dec. 28, 2017

(86) PCT No.: PCT/JP2017/047152
§ 371 (c)(1),
(2) Date: Jun. 28, 2019

(87) PCT Pub. No.: WO2018/124258
PCT Pub. Date: Jul. 5, 2018

(65) Prior Publication Data
US 2019/0343161 A1 Nov. 14, 2019

(30) Foreign Application Priority Data

Dec. 28, 2016 (JP) .............................. JP2016-254992
May 11, 2017 (JP) .............................. JP2017-094783

(51) Int. Cl.
| | |
|---|---|
| *A61K 36/31* | (2006.01) |
| *A23L 33/105* | (2016.01) |
| *A61P 3/02* | (2006.01) |
| *A61P 25/04* | (2006.01) |
| *A61K 31/26* | (2006.01) |

(52) U.S. Cl.
CPC ............ *A23L 33/105* (2016.08); *A61K 31/26* (2013.01); *A61K 36/31* (2013.01); *A61P 3/02* (2018.01); *A61P 25/04* (2018.01)

(58) Field of Classification Search
None
See application file for complete search history.

(56) References Cited

U.S. PATENT DOCUMENTS

| | | | |
|---|---|---|---|
| 10,471,038 B2 * | 11/2019 | Nabeshima ............ | A61K 31/26 |
| 2003/0064131 A1 | 4/2003 | Murata et al. | |
| 2015/0196525 A1 * | 7/2015 | Cornblatt .................. | A61P 3/06 424/475 |
| 2016/0243057 A1 * | 8/2016 | McWherter ............ | A61K 31/05 |

FOREIGN PATENT DOCUMENTS

| | | | |
|---|---|---|---|
| JP | 200381939 A | | 3/2003 |
| JP | 2009/155334 | * | 7/2009 |
| JP | 2009155333 A | | 7/2009 |
| JP | 2010280573 A | | 12/2010 |
| WO | 2010086972 A1 | | 8/2010 |
| WO | 2010140271 A1 | | 12/2010 |
| WO | WO 2010/140271 | * | 12/2010 |

OTHER PUBLICATIONS

Reeves et al., "Identification of ambiguities in the 1994 chronic fatigue syndrome research case definition and recommendations for resolution," BMC Health Services Research, vol. 3, issue 1, p. 25, 2003 (9 pages).
"Survey of chronic fatigue syndrome and verification and widespread use of objective diagnostic procedure for the same," Research Team, Explanation of chronic fatigue syndrome (CFS) diagnostic criteria (revised on Mar. 2013) with partial English translation (30 pages).
"Progress in Medicine," vol. 30, pp. 505-510, 2010; with partial English translation (6 pages).
Nippon Shokuhin Kagaku Kogaku, vol. 51, No. 9, 477-482, 2004 (6 pages).
Kawai et al., "Chronic fatigue syndrome—Review by our cases and documents," 1992, Japanese Medical Journal; with partial English translation (8 pages).
K. Yoshihara, "Psychosomatic disorder and functional somatic syndrome," 2015, Japanese Journal of Psychosomatic Internal Medicine; with partial English translation (9 pages).
Y. Matsumoto, "Analysis for clinical course and prognosis (QOL) of chronic fatigue syndrome (including fibromyalgia syndrome)," 2002; with partial English translation (4 pages).
International Search Report issued in International Application No. PCT/JP2017/047152; dated Feb. 6, 2018 (5 pages).
Written Opinion of the International Searching Authority issued in International Application No. PCT/JP2017/047152; dated Feb. 6, 2018 (4 pages).

* cited by examiner

*Primary Examiner* — Ralph J Gitomer
(74) *Attorney, Agent, or Firm* — Osha Bergman Watanabe & Burton LLP

(57) ABSTRACT

The present invention can provide: a prophylactic or ameliorating/therapeutic agent for chronic fatigue syndrome, idiopathic chronic fatigue and fibromyalgia, which contains a processed product of Japanese horseradish (wasabi) as an active ingredient; a food, a beverage, a medicine or a cosmetic, and a medicine for preventing or ameliorating/treating diseases relating to chronic fatigue syndrome, idiopathic chronic fatigue and fibromyalgia, each of which contains the processed product of wasabi; and methods for using these products.

2 Claims, 2 Drawing Sheets

Fig. 2

Levels of fatigue/malaise on the basis of PS (performance status)

| | |
|---|---|
| 0. | Can have comfortable life without malaise and act without any limitation. |
| 1. | Able to participate in regular social activities and do work, but frequently experiences malaise. |
| 2. | Able to participate in regular social activities and do work, but frequently requires rest because of general malaise. |
| 3. | Unable to participate in social activities and do work for several days a month because of general malaise, and thus requires rest at home. |
| 4. | Unable to participate in social activities and do work for several days a week because of general malaise, and thus requires rest at home. |
| 5. | Difficult to perform ordinary social activities and doing work. Able to do light work, but requires rest at home for several days a week. |
| 6. | Able to do light work on a day when a subject is in a good condition, but takes rest at home more than half a week. |
| 7. | Able to take care of a subject's personal needs and requires no assistance, but unable to participate in regular social activities and do light work. |
| 8. | Able to take care of a subject's personal needs to some extent, but requires assistance frequently and stays in bed more than half a day. |
| 9. | Unable to take care of a subject's personal needs, always requires assistance and requires to stay in bed 24 hr/day. |

US 10,925,304 B2

METHOD FOR TREATING CHRONIC FATIGUE SYNDROME, IDIOPATHIC CHRONIC FATIGUE, AND FIBROMYALGIA

TECHNICAL FIELD

The present invention relates to a prophylactic or improving/therapeutic agent for chronic fatigue syndrome, idiopathic chronic fatigue, and fibromyalgia, comprising a processed wasabi product as an active ingredient, a food or a beverage, a drug or a cosmetic and a drug for preventing or improving/treating diseases relating to chronic fatigue syndrome, idiopathic chronic fatigue, and fibromyalgia, containing the processed wasabi product, as well as a method for using them.

BACKGROUND ART

Lassitude and malaise are sensations that everyone experiences routinely. A complaint, "feeling languid" is ranked high every year on the rate of persons with subjective symptoms of "Comprehensive Survey of Living Conditions" conducted by the Ministry of Health, Labour and Welfare.

The term "chronic fatigue" refers to all subjective lassitude lasting for more than half a year, regardless of the degree of lassitude, the presence or the absence of symptoms other than lassitude, and being affected or not affected with a disease. Even subtle lassitude, which does not interfere with daily life, is referred to as chronic fatigue when it is lasting for more than half a year.

Meanwhile, chronic fatigue syndrome is a disease that is diagnosed on the basis of the diagnostic criteria etc., for chronic fatigue syndrome of the CDC (Centers for Disease Control and Prevention) and the Ministry of Health, Labour and Welfare (2013), and is distinguished from "chronic fatigue" (Non Patent Documents 1 and 2).

Chronic fatigue syndrome is a disease such that a person who has lived a healthy life has a sudden attack of unexplained intense systemic malaise, which is triggered by interpersonal, physical, chemical, and biological combined stresses, followed by intense lassitude as well as slight fever, lymphadenopathy, muscle pain, joint pain, headache, decreased thinking ability, sleep disorder, etc., lasting for at least 6 months, and then will be unable to live a sound social life.

Patent Document 1 states that 6-methylthiohexyl isothiocyanate contained in wasabi has an effect of enhancing cerebral α wave, a relaxing effect, an effect of enhancing concentration, and an anti-stress effect.

Patent Document 2 describes a method for producing an allyl isothiocyanate-free isothiocyanate-containing food material, which involves retaining pulverized plants of the family Brassicaceae comprising Japanese horseradish and/or Western horseradish at temperatures ranging from −3° C. to 50° C. for a time period sufficient for an enzyme reaction to take place, generating isothiocyanates containing a pungent component, allyl isothiocyanate, and then subjecting the isothiocyanates to an aeration or suction step, a drying step, or a combination of these steps, so as to remove volatile allyl isothiocyanate.

Non Patent Document 3 describes the therapeutic effects of Middle-Reinforcing and Qi-Benefiting Decoction (Hochuekkito) to be taken twice a day on a patient diagnosed with chronic fatigue syndrome on the basis of the CSF diagnostic criteria and having a PS value of at least 2.

Although symptomatic treatments using Chinese medicines, vitamins, or psychotropic drugs are available for the treatment of chronic fatigue syndrome, however, there is no specific drug for treatment thereof and the symptoms persist and are not improved even after various treatments in most cases.

PRIOR ART DOCUMENTS

Patent Document

Patent Document 1: JP No. 2010-280573
Patent Document 2: JP No. 2003-81939

Non Patent Document

Non Patent Document 1: Reeves W C et al.: Identification of ambiguities in the 1994 chronic fatigue syndrome research case definition and recommendations for resolution. BMC Health Sery Res. 3(1):25, 2003.
Non Patent Document 2: "Survey of chronic fatigue syndrome and verification and widespread use of objective diagnostic procedure for the same" Research Team. Explanation of "chronic fatigue syndrome (CFS) diagnostic criteria (revised on March 2013)
Non Patent Document 3: Progress in Medicine 30: 505-510, 2010.
Non Patent Document 4: Nippon Shokuhin Kagaku Kogaku, Vol. 51, No. 9, 477-482 (2004)

SUMMARY OF INVENTION

Technical Problem

An object to be achieved by the present invention is to provide a prophylactic or improving/therapeutic agent for chronic fatigue syndrome, idiopathic chronic fatigue, and fibromyalgia, comprising a processed wasabi product as an active ingredient, and a food or a beverage, a drug or a cosmetic, and a drug for preventing or improving/treating diseases relating to chronic fatigue syndrome, idiopathic chronic fatigue, and fibromyalgia, containing the agent, as well as a method for using them.

Solution to Problem

As a result of intensive studies to achieve the above object, the present inventors have discovered that a processed wasabi product can improve symptoms that do not respond to any treatment with Chinese medicines, vitamins, or psychotropic drugs, and can decrease the drugs for which side effects due to long-term administration are of concern, and thus have completed the present invention.

Advantageous Effects of Invention

The present invention can provide a prophylactic or improving/therapeutic agent for chronic fatigue syndrome, idiopathic chronic fatigue, and fibromyalgia, comprising a processed wasabi product as an active ingredient, a food or a beverage, a drug or a cosmetic, and a drug for preventing or improving/treating diseases relating to chronic fatigue syndrome, idiopathic chronic fatigue, and fibromyalgia, containing the agent, as well as a method for using them.

BRIEF DESCRIPTION OF DRAWINGS

FIG. 2 shows the degree of fatigue/malaise as determined on the basis of the PS (performance status).

DESCRIPTION OF EMBODIMENTS

Figure 1:
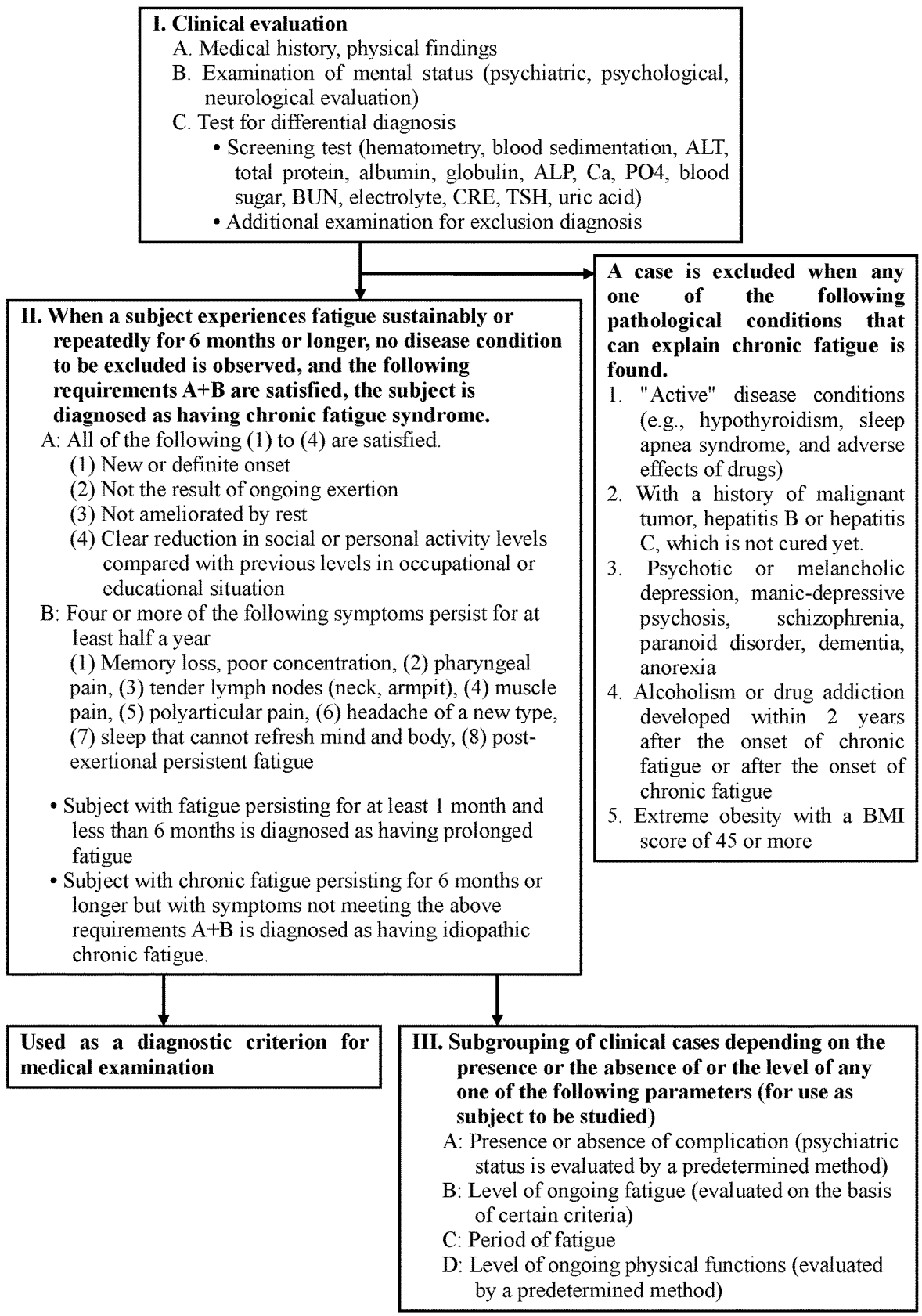
FIG. 1 shows diagnostic procedures for chronic fatigue syndrome of the CDC (Centers for Disease Control and Prevention).

The present invention is described in detail below.

<Processed Wasabi Product>

In the present invention, a processed wasabi product can be prepared or produced from the whole or each site of the above wasabi. Examples of each site include flower, spikes, stems, leaves, branches, branches and leaves, trunks, bark, rhizome, root bark, roots, seeds, nutgalls, heartwood, aboveground parts, and underground parts. Particularly, rhizome is preferable. Moreover, a method for preparing or producing a processed wasabi product is not particularly limited, and, for example, the product can be prepared or produced by a generally employed method.

In the present invention, the lower limit of the content of a ω-methylsulfinylalkyl isothiocyanate with respect to the total weight of a processed wasabi product is 0.00050 wt % and preferably 0.0025 wt %, for example. Furthermore, the upper limit of the same is 0.425 wt % and preferably 0.40 wt %, for example. Moreover, the upper limit and the lower limit can be used in combination as appropriate. More specifically, the w-methylsulfinylalkyl isothiocyanate content with respect to the total weight of the processed product of a plant of the genus *Wasabia* ranges from 0.00050 wt % to 0.425 wt %, and preferably 0.0025 wt % to 0.40 wt %, for example. Further, the ω-methylsulfinylalkyl isothiocyanate content can be measured by gas chromatography, for example.

In the present invention, examples of a processed wasabi product include pulverized products, extracts and dried products of the above wasabi. Such pulverized wasabi products, wasabi extracts and dried products thereof can be prepared or produced, for example, by pulverizing directly or after cutting each site of the plants of the genus Wasabi, such as roots, stems, leaves, flower buds, flowers and barks into an appropriate size, then, juicing, and extracting with solvents, and if necessary, by drying them. Furthermore, a processed wasabi product can also be prepared or produced by mixing one or more sites of wasabi.

In the present invention, for preparation or production of a wasabi extract, for example, water, an organic solvent or a mixture thereof can be used as a solvent for extraction. Examples of the organic solvent include lower alcohols such as methanol and ethanol, chloroform, ethyl acetate, and n-hexane, and preferable examples thereof include methanol and ethanol. Furthermore, two or more of these organic solvents can also be mixed and used.

In the present invention, the amount of a solvent to be used for extraction can be adequately selected depending on the type and the site of wasabi, and the type of a solvent for extraction, for example. The weight ratio of wasabi and a solvent for extraction is, for example, 1:0.5 to 1:2. Moreover, the extraction time is, for example, 0.5 to 2 hours. The temperature for extraction is, for example, room temperature. The extraction method is not particularly limited. For example, an arbitrary method such as batch extraction or successive extraction involving column extraction can be employed.

In the present invention, the wasabi extract obtained can be used as it is. Furthermore, purification treatment can be additionally performed as needed. The purification treatment may be performed by a general method. For example, the wasabi extract can be purified by filtration according to a standard method. Subsequently, the filtrate obtained can be concentrated under reduced pressure and lyophilized to obtain the wasabi extract according to the present invention.

In the present invention, for example, a rhizome extract of Japanese horseradish or a dried product thereof can be used as a processed wasabi product. Such a rhizome extract of Japanese horseradish or a dried product thereof can be prepared and produced, for example, by extracting the rhizome of Japanese horseradish with water or a lower alcohol such as methanol and ethanol, filtrating and concentrating, if necessary, adding excipients and the like, and drying the resultant.

In the present invention, a processed wasabi product is produced by maintaining pulverized plants of the family Brassicaceae comprising Japanese horseradish and/or Western horseradish at temperatures ranging from −3° C. to 50° C. for a time period sufficient for enzymatic reaction, so as to generate isothiocyanates containing a pungent component, allyl isothiocyanate, and then subjecting the isothiocyanates to an aeration or suction step, or a drying step, or further a combination of these steps to remove volatile allyl isothiocyanate.

In the present invention, the processed wasabi product is particularly preferably a Japanese horseradish extract, which is a processed wasabi rhizome product. The Japanese horseradish extract is, for example, an acetone extract of the pulverized product of Japanese horseradish rhizome which contains 1.0 wt % to 4.0 wt % of 6-methylsulfinylhexyl isothiocyanate as an active ingredient. The Japanese horseradish extract preferably does not contain volatile arylsulfinyl but preferably contains 6-methylsulfinylhexyl isothiocyanate as a sole active ingredient.

<ω-Methylsulfinylalkyl Isothiocyanate>

In the present invention, the ω-methylsulfinylalkyl isothiocyanate may be a chemically synthesized substance, or, a natural product as an extract obtained from a plant of the family Brassicaceae.

In the present invention, when the ω-methylsulfinylalkyl isothiocyanate is a natural product, the ω-methylsulfinylalkyl isothiocyanate can be obtained from one or more selected from the group of plants of the family Brassicaceae including Japanese horseradish, Western horseradish, cabbage, watercress, Brussels sprouts, cauliflower, radish, Karami Daikon (*Raphanus sativus* L. var. *longipinnatus* L. H. Bailey), rape seed, broccoli, Takana (*Brassica juncea* var. *integrifolia*), Indian mustard, turnip, and Chinese cabbage. A preferable example is Japanese horseradish (*Wasabia Japonica*) with a high content of 6-methylsulfinylhexyl isothiocyanate. In Japanese horseradish, for example, leaves and/or rhizome can be used and preferably rhizome can be used.

A method for preparing the ω-methylsulfinylalkyl isothiocyanate is, for example, as described below.

For example, upon extraction from a plant of the family Brassicaceae containing the ω-methylsulfinylalkyl isothiocyanate, the plant body is preferably subjected to pretreatment for extraction using physical measures such as pulverization or grating, and then to extraction with water or an organic solvent such as methanol, ethanol, acetone, ethyl acetate, diethyl ether, dichloromethane, and dichloroethane, or extraction by a distillation method such as steam distillation or molecular distillation. However, methods for extraction are not particularly limited to these methods.

For example, a specific extraction method of Japanese horseradish with an organic solvent is as follows. A rhizome of Japanese horseradish is grated, extracted with an ethyl acetate solvent, dehydrated with anhydrous sodium sulfate, and then concentrated using an evaporator to obtain the ω-methylsulfinylalkyl isothiocyanate. This method is particularly optimum for extraction of 6-methylsulfinylhexyl isothiocyanate. Commercially available 6-methylsulfinylhexyl isothiocyanate can be used. An example thereof is Wasabi sulfinyl (registered trademark) (6-MSITC) produced by KINJIRUSHI WASABI INTERNATIONAL CO., LTD.

For example, when the ω-methylsulfinylalkyl isothiocyanate is extracted from watercress, extraction is performed in the same manner as in the case of Japanese horseradish. For example, watercress is ground, extracted with an ethyl acetate solvent, dehydrated with anhydrous sodium sulfate, and then concentrated using an evaporator to obtain the ω-methylsulfinylalkyl isothiocyanate. This method is particularly optimum for extraction of 7-methylsulfinylheptyl isothiocyanate or 8-methylsulfinyloctyl isothiocyanate.

Note that the above extract is purified, after extraction and concentration, by an arbitrary method such as liquid-liquid distribution, chromatography, molecular distillation, or rectification. Before and after the purification means, drying means such as hot air drying and lyophilization may be used in combination.

In the present invention, examples of the ω-methylsulfinylalkyl isothiocyanate include allyl isothiocyanate, secondary butyl isothiocyanate, 3-butenyl isothiocyanate, 4-pentenyl isothiocyanate, 5-hexenyl isothiocyanate, 5-(methylthio)pentyl isothiocyanate, 6-methylthiohexyl isothiocyanate, 7-(methylthio)heptyl isothiocyanate, 8-methylthiooctyl isothiocyanate, 4-methyl sulfinylbutyl isothiocyanate, 5-methylsulfinylpentyl isothiocyanate, 6-methylsulfinylhexyl isothiocyanate, 7-methylsulfinylheptyl isothiocyanate, and 8-methylsulfinyloctyl isothiocyanate. Preferable examples of the same include preferably 4-methylsulfinylbutyl isothiocyanate, 5-methylsulfinylpentyl isothiocyanate, 6-methylsulfinylhexyl isothiocyanate, 7-methylsulfinylheptyl isothiocyanate and 8-methylsulfinyloctyl isothiocyanate, and further preferably 6-methylsulfinylhexyl isothiocyanate.

In the present invention, the ω-methylsulfinylalkyl isothiocyanate can also be synthesized by various chemical synthesis methods in addition to extraction from a plant body by the above methods. Persons skilled in the art can synthesize these active ingredients by methods known in the art.

For example, according to the method of Kiaer et al., (Kiaer et al. Acta chem. Scand, 11, 1298, 1957), ω-chloroalkenol is used as a starting material, refluxed with $CH_3SNa$ to obtain ω-methylthioalkenol, and then $SOCl_2$ is acted thereon to obtain ω-chloroalkenol methyl sulfide.

For example, next, an amino group is introduced using Gabriel method to generate N-(w-methylthioalkyl)-phthalimide, and then hydrazine hydrate is added to the resultant and refluxed to obtain ω-methylthioalkyl amine. Moreover, according to the method of Li et al. (Li et al., J. Org. Chem., 62, 4539, 1997), a methylthio group of a ω-methylthioalkyl isothiocyanate obtained via thiuram disulfide is oxidized with mCPBA to obtain the ω-methylsulfinylalkyl isothiocyanate is obtained.

In the present invention, the term "physiologically acceptable salt" refers to a salt retaining physiological effects and retaining the properties of a free base or a free acid that is not undesirable because of physiological or other reasons. In the present invention, examples of the physiologically acceptable salt include a pharmaceutically acceptable salt.

<Foods or Beverages (Foods with Function Claims, Foods for Specified Health Uses), Drugs, and Cosmetics Comprising, as an Active Ingredient and/or Additive, a Prophylactic or Improving/Therapeutic Agent for Chronic Fatigue Syndrome, Idiopathic Chronic Fatigue, and Fibromyalgia Containing a Processed Wasabi Product as Active Ingredients>

In the present invention, a processed wasabi product itself can be used as a prophylactic or improving/therapeutic agent for chronic fatigue syndrome, idiopathic chronic fatigue, and fibromyalgia. Furthermore, the prophylactic or improving/therapeutic agent for chronic fatigue syndrome, idiopathic chronic fatigue, and fibromyalgia comprising a processed wasabi product of the present invention, as an active ingredient can be incorporated in a food or a beverage (foods with function claims, foods for specified health uses), a drug, or a cosmetic. Moreover, one aspect of the present invention is a food or a beverage (foods with function claims, foods for specified health uses), a drug, or a cosmetic comprising the prophylactic or improving/therapeutic agent as an active ingredient and/or additive. Examples of a preferred aspect of the present invention include oral drugs (including oral quasi drugs) and a food or a beverage containing the prophylactic or improving/therapeutic agent of the present invention.

When the prophylactic or improving/therapeutic agent for chronic fatigue syndrome, idiopathic chronic fatigue, and fibromyalgia of the present invention is incorporated in a food or a beverage, in addition to the prophylactic or improving/therapeutic agent of the present invention, a sweetener, a colorant, a preservative, a thickener, a stabilizer, a gelatinizing agent, a sizing agent, an antioxidant, a color coupler, a bleaching agent, a fungicide (anti-mold agent), a yeast food, a gum base, a fragrance, an acidulant, a seasoning, an emulsifier, a pH adjusting agent, brine, a leavening agent, a nutrition-reinforcing agent, or other food or beverage materials, etc., may be mixed to prepare the food or the beverage in a desired form. There are no particular limitations on the form of the food or the beverage containing the prophylactic or improving/therapeutic agent of the present invention. Examples thereof include: supplement type foods such as gels, granules, grains, capsules, tablets, powders, liquids or semi-solids; beverages such as carbonated beverages, soft beverages, milk-based beverages, alcoholic beverages, fruit-based beverages; teas or nutrient beverages; powdered beverages such as powdered juice or powdered soup; confectioneries such as chewing gum; tablets, candies, cookies, gumdrops, rice crackers, biscuits and jelly; as well as bread, noodles, cereal, jam and condiments. These foods can be used as, for example, ordinary foods or beverages as well as neutraceuticals such as nutritional supplements, functional foods, foods for specified health uses, or foods for invalids. These foods or beverages are used as foods or beverages for preventing improving/treating chronic fatigue syndrome, idiopathic chronic fatigue, and fibromyalgia, for example.

When the prophylactic or improving/therapeutic agent for chronic fatigue syndrome, idiopathic chronic fatigue, and fibromyalgia of the present invention is incorporated in a drug (including quasi drugs), in addition to the prophylactic or improving/therapeutic agent of the present invention, other medicinal ingredients, pharmaceutically acceptable carriers, additives and the like may be incorporated arbitrarily as needed. Examples of pharmaceutically acceptable carriers and additives include binders, disintegrants, lubricants, wetting agents, buffering agents, preservatives, and fragrances. There are no particular limitations on the form of a drug containing the prophylactic or improving/therapeutic agent of the present invention. Examples of the form include injections, external preparations, inhalers, suppositories, film agents, troches, liquids, powders, tablets, granules, capsules, syrups, eye drops, eyewashes, and nasal drops. In addition, a form suitable for oral administration (namely, an orally administered drug) is preferable, and examples thereof include troches, liquids, powders, tablets, granules, capsules and syrups. These drugs (including quasi-drugs) are used as the prophylactic or improving/therapeutic drugs for chronic fatigue syndrome, idiopathic chronic fatigue, and fibromyalgia of the present invention.

When the prophylactic or improving/therapeutic agent for chronic fatigue syndrome, idiopathic chronic fatigue, and fibromyalgia of the present invention is incorporated in a cosmetic (including functional cosmetics) or quasi-drug for external use, a pharmaceutically or cosmetologically acceptable carrier (such as water or an oily component) can be incorporated in addition to the prophylactic or improving/therapeutic agent of the present invention and prepared into a desired form. There are no particular limitations on the form of the cosmetic provided it can be applied to the skin. Examples of cosmetic forms include liquids, milky lotions, powders, solids, suspensions, creams, ointments, mousses, granules, tablets, gels, jellies, pastes, gelatins, aerosols, sprays, liniments and packs. These cosmetics are used as cosmetics for preventing or improving/treating chronic fatigue syndrome, idiopathic chronic fatigue, and fibromyalgia.

Furthermore, the prophylactic or improving/therapeutic agent for chronic fatigue syndrome, idiopathic chronic fatigue, and fibromyalgia of the present invention can also be used as an active ingredient and/or additive for foods or beverages, drugs (including quasi drugs) or cosmetics. Through the use of a food or a beverage, a drug (including quasi drug), or a cosmetic containing the prophylactic or improving/therapeutic agent of the present invention, the effect resulting from prevention or improvement/treatment of chronic fatigue syndrome, idiopathic chronic fatigue, and fibromyalgia according to the present invention can be obtained. The prophylactic or improving/therapeutic agent of the present invention is incorporated in a food or a beverage, a drug (including quasi drugs) or a cosmetic, so that the effect of preventing improving/treating chronic fatigue syndrome, idiopathic chronic fatigue, and fibromyalgia can be imparted to the resulting product. The prophylactic or improving/therapeutic agent for chronic fatigue syndrome, idiopathic chronic fatigue, and fibromyalgia of the present invention can be used for imparting functions for preventing improving/treating chronic fatigue syndrome, idiopathic chronic fatigue, and fibromyalgia to oral drugs (including oral quasi drugs) and foods or beverages.

When the prophylactic or improving/therapeutic agent for chronic fatigue syndrome, idiopathic chronic fatigue, and fibromyalgia of the present invention is used as an additive, there are no limitations on the form or the like of a food or a beverage, a drug (including quasi drug), a cosmetic, in which the additive is incorporated and examples thereof include the above-mentioned food or beverage, drug (including quasi drug), and cosmetic forms.

There are no particular limitations on the amount of the prophylactic or improving/therapeutic agent of the present invention to be incorporated in a food or a beverage, a drug (including quasi-drugs) or a cosmetic, and the amount is suitably set depending on the objective of application (such as the type of a target disease or symptoms), an application target site, the gender and age of a subject, and the food or beverage, drug (including quasi-drugs) or cosmetic form, administration or ingestion method and the number of administrations thereof or preference, for example. Thus, although there are no limitations on the amount of the prophylactic or improving/therapeutic agent or the like of the present invention to be incorporated in a food or a beverage, a drug (including quasi-drug) or a cosmetic, the daily adult dosage of the prophylactic or improving/therapeutic agent, or the like of the present invention, in terms of the total amount of the aforementioned methylsulfinylalkyl isothiocyanate incorporated, ranges from 0.1 mg to 100 mg, preferably 0.1 mg to 70 mg, more preferably 0.5 mg to 50 mg and particularly preferably 0.5 mg to 30 mg, for example. In addition, as was previously described, the aforementioned methylsulfinylalkyl isothiocyanate is obtained by extraction and purification from a plant of the Brassicaceae family, such as Japanese horseradish, Western horseradish, cabbage, watercress, Brussels sprouts, cauliflower, radish, Karami Daikon (*Raphanus sativus* L. var. *longipinnatus* L. H. Bailey), rape seed, broccoli, Takana (*Brassica juncea* var. *integrifolia*), Indian mustard, turnip, or Chinese cabbage. Moreover, these components can also be obtained from a plant via extraction and purification treatment, and an extract per se obtained in this process may be used as the prophylactic or improving/therapeutic agent of the present invention. When a processed wasabi product per se is used as the prophylactic or improving/therapeutic agent of the present invention, an extract is desirably incorporated in a food or a beverage, a drug (including quasi-drugs) or a cosmetic, as a daily adult dosage, within the range of 0.01 g to 1.0 g, preferably 0.01 g to 0.7 g, more preferably 0.05 g to 0.5 g, and particularly preferably 0.05 g to 0.3 g.

<Composition>

The present invention also relates to a composition containing a processed wasabi product, the ω-methylsulfinylalkyl isothiocyanate or a physiologically acceptable salt thereof as an active ingredient. The description of foods or beverages, drugs or cosmetics of the present invention is also applicable to a food or beverage, drug or cosmetic composition of the present invention.

The food or beverage, drug or cosmetic composition of the present invention contains a processed wasabi product in an amount, for example, ranging from 0.1 wt % to 85.0 wt %, and preferably 0.5 wt % to 80.0 wt %, defined the total weight as 100 wt %.

The food or beverage, drug or cosmetic composition of the present invention contains the ω-methylsulfinylalkyl isothiocyanate or a physiologically acceptable salt thereof in an amount, for example, ranging from 0.00050 wt % to 0.425 wt %, and preferably 0.0025 wt % to 0.40 wt %, defined the total weight as 100 wt %.

The food or beverage, drug or cosmetic composition of the present invention contains, for example, 0.1 wt % to 85.0 wt %, preferably 0.5 wt % to 80.0 wt % of a plant extract (e.g., a processed wasabi product) containing an ω-methylsulfinylalkyl isothiocyanate or a physiologically acceptable salt thereof, defined the total weight as 100 wt %.

The food or beverage, drug or cosmetic composition of the present invention contains, for example, 15.0 wt % to 99.9 wt %, and preferably 20.0 wt % to 99.5 wt %, of a physiologically acceptable additive, defined the total weight as 100 wt %.

There are no particular limitations on the additive in the food or beverage, drug or cosmetic composition of the present invention, provided that it is a physiologically inert, inorganic or organic additive. An additive such as lactose, cornstarch or a derivative thereof, talc, stearic acid or a salt thereof, oligosaccharide, HPMC, titanium oxide, reduced maltose syrup, edible purified processed oils and fats, vitamin C, cellulose, fragrance, cyclodextrin, citric acid or vitamin B12 can be used as such an additive for tablets, sugar-coated tablets or hard gelatin capsules, for example.

Examples of suitable additives for soft gelatin capsules include vegetable oils, waxes, fats and semi-solid or liquid polyols. Examples of suitable additives for production of liquids or syrups include water, polyols, sucrose, inverted sugars and dextrose. Examples of additives suitable for injection preparations include water, alcohols, polyols, glycerol and vegetable oils. Examples of additives suitable for suppositories include natural or hardened oils, waxes, fats and semi-liquid or liquid polyols.

<Use>

The prophylactic or improving/therapeutic agent for chronic fatigue syndrome, idiopathic chronic fatigue, and fibromyalgia, the food or the beverage, the drug, or the cosmetic, and the food or beverage, drug or cosmetic composition of the present invention can be used for the following uses, for example.

In the present invention, the expression "improving/treating chronic fatigue syndrome" refers to decreasing the dosage of a drug (e.g., antibiotics, anti-inflammatory agents, and psychotropic agents) or improvement of PS value (amount of activity) or improvement of subjective symptoms.

In the present invention, statements such as "relieves temporary physical lassitude during the course of daily life", "relieves physical lassitude occurring by exercise", or statements similar thereto can be displayed on products relating to the prevention or improvement/treatment of chronic fatigue syndrome, idiopathic chronic fatigue, and fibromyalgia of the present invention, the product packages, product information or product advertisements (such as transaction documents, usage instructions, product inserts, or catalogs and Internet web sites used for mail-order sales).

EXAMPLES

The present invention will be described with reference to Reference Example, Examples and Preparation Examples below; however, the present invention is not limited to these Examples and Preparation Examples.

Reference Example: Preparation of Japanese Horseradish Extract 1.0 kg of Japanese horseradish was frozen and then freeze-pulverized. The pulverized Japanese horseradish was added into a glass container, and then left to stand at 40° C. for 1 hour to cause an enzymatic reaction. After the completion of the reaction, air within the container was suctioned to remove most of allyl isothiocyanate that is a volatile component. After addition of 5 liters of acetone into the container, the resultant was stirred for 1 hour and then filtered to obtain an extract. The extract was concentrated to obtain 55 g of a concentrate, the concentrate was adsorbed to 100 g of dextrin, and then dried to obtain a powdered material. The concentrate was subjected to GC analysis (analyzed with reference to the conditions of Non Patent Document 4), confirming that the concentrate contained 6-methylsulfinylhexyl isothiocyanate as a major ingredient.

Example 1: Therapeutic Effect of Processed Wasabi Product on Chronic Fatigue Syndrome Patient 1

To Patient 1 meeting the diagnostic criteria for chronic fatigue syndrome according to the CDC (Centers for Disease Control and Prevention) and the Ministry of Health, Labour and Welfare (2013), an antibiotic <ciprofloxacin, administered at a dose of 600 mg/day for 1 or 2 weeks per month> was prescribed for neck pain by local otolaryngologist. Subsequently, "Wasabi no iyashi (registered trademark, Kobe Wellness Science Co., Ltd.)" was administered 1 capsule/day, so that the frequency of the use of the antibiotic was reduced by half.

Patient 2

Patient 2 meeting the diagnostic criteria for chronic fatigue syndrome according to the CDC (Centers for Disease Control and Prevention) and the Ministry of Health, Labour and Welfare (2013) had slight fever, hot feeling, and exertional malaise which had not been improved by treatment with a Chinese medicine (7.5 g of coix seed decoction (Yokuininto)), a psychotropic drug (20 mg of duloxetine hydrochloride), and an antiinflammatory agent (100 mg of Celecoxib). However, through administration of 7.5 g of Bupleurum and Cassia Twig Decoction (Saikokeishito) (before dispersion) instead of the coix seed decoction and administration of the "Wasabi no iyashi (registered trademark, Kobe Wellness Science Co., Ltd.) 1 capsule/day, symptoms of slight fever and hot feeling disappeared. This enabled discontinuation of the administration of a psychotropic drug (duloxetine hydrochloride).

Patient 3

Patient 3 meeting the diagnostic criteria for chronic fatigue syndrome according to the CDC (Centers for Disease Control and Prevention), the Ministry of Health, Labour and Welfare (2013) and the diagnostic criteria for fibromyalgia according to the American College of Rheumatology (2010) had symptoms such as back pain, decreased thinking ability, and difficulty in waking up persisting even after administration of a Chinese medicine (7.5 g of Middle-Reinforcing and Qi-Benefiting Decoction (Hochuekkito)), a psychotropic drug (75 mg of sertraline hydrochloride, and 5 mg of nortriptyline hydrochloride). However, the symptoms subsided through administration of Wasabi no iyashi (registered trademark, Kobe Wellness Science Co., Ltd.) 1 capsule/day.

Patient 4

Patient 4 meeting the diagnostic criteria for chronic fatigue syndrome according to the CDC (Centers for Disease Control and Prevention) and the Ministry of Health, Labour and Welfare (2013) had flu-like symptoms such as malaise, headache dull, and nasal discharge persisting even after treatment with a Chinese medicine (7.5 g of *Angelica* and Peony Powder (Tokishakuyakusan)), 1500 mg of vitamin C, and a psychotropic drug (50 mg of sertraline hydrochloride and 25 mg of trazodone hydrochloride). Through administration of Wasabi no iyashi (registered trademark, Kobe Wellness Science Co., Ltd.) 1 capsule/day, patient 4 had such flu-like symptoms less frequently and exhibited the increased amount of activity. PS was improved from 6 to 5.

Patient 5

Patient 5 meeting the diagnostic criteria for chronic fatigue syndrome according to the CDC (Centers for Disease Control and Prevention) and the Ministry of Health, Labour and Welfare (2013) tended to be bedridden because of slight fever and exertional malaise that had not been improved by treatment with a Chinese medicine (7.5 g of Minor Bupleurum Decoction (Shosaikoto)) and a psychotropic drug (40 mg of duloxetine hydrochloride). However, the symptoms were improved through administration of Wasabi no iyashi (registered trademark, Kobe Wellness Science Co., Ltd.) 3 capsules/day, thereby increasing the time to be able to spend outdoors. PS was improved from 7 to 6.

Patient 6

Patient 6 meeting the diagnostic criteria for chronic fatigue syndrome according to the CDC (Centers for Disease Control and Prevention) and the Ministry of Health, Labour and Welfare (2013) had depression that was improving due to treatment with an antidepressant drug (20 mg of duloxetine hydrochloride), but was unable to do his/her work sufficiently because of exertional malaise, regularly took a portion of 60 mg of loxoprofen sodium hydrate almost every day because of his or her persisting headache. Through administration of Wasabi no iyashi (registered trademark, Kobe Wellness Science Co., Ltd.) 1 capsule/day, headache was alleviated, an analgesic agent was less frequently used.

Example 2. Therapeutic Effect of Processed Wasabi Product on Chronic Fatigue Syndrome To each of 17 patients meeting the diagnostic criteria for chronic fatigue syndrome according to the CDC (Centers for Disease Control and Prevention) and the Ministry of Health, Labour and Welfare (2013), Wasabi no iyashi (registered trademark, Kobe Wellness Science Co., Ltd.) (1 capsule: wasabi supplement) was administered.

TABLE 1

|  | Wasabi supplement |
| --- | --- |
| The number of patients with improved symptoms | 6 |

Patients who exhibited the following conditions were determined to have improved symptoms.
  Decreased doses of antibiotics, psychotropic drugs, or anti-inflammatory drugs
  Improvement in PS value (amount of activity)
  Improvement in subjective symptoms Example 3. Therapeutic Effect of Processed Wasabi Product on Idiopathic Chronic Fatigue Patient 7
To patient 7 having unexplained chronic fatigue and meeting the diagnostic criteria for idiopathic chronic fatigue according to the CDC (Centers for Disease Control and Prevention) and the Ministry of Health, Labour and Welfare (2013), Wasabi no iyashi (registered trademark, Kobe Wellness Science Co., Ltd.), was administered 1 capsule/day. This alleviated headache dull and "cleared the patient's head".

Patient 8
Patient 8 had repeated absence from work and reinstatement because of recurrent depression. A step such as limitation of overtime work was taken because of unstable symptoms. Patient 8 started to take Wasabi no iyashi (registered trademark, Kobe Wellness Science Co., Ltd.) 1 capsule/day and now is doing his/her work without aggravating the symptoms even when the work load is increased.

Prescription Example

Prescription Example 1: Capsules

| Japanese horseradish extract/oligosaccharide | 79 wt % |
| --- | --- |
| Calcium stearate | 3 wt % |
| HPMC/titanium oxide | 18 wt % |

A composition (330 mg) prepared by mixing as described above was encapsulated into capsules, thereby producing capsules.

Prescription Example 2: Tablets

| Japanese horseradish extract/oligosaccharide | 0.9 wt % |
| --- | --- |
| Reduced malt sugar syrup | 55 wt % |
| Edible purified processed oils and fats | 4.0 wt % |
| Vitamin C | 24 wt % |
| Cellulose | 10 wt % |
| Fragrance | 2.0 wt % |
| Calcium stearate | 1.5 wt % |
| Cyclodextrin | 1.4 wt % |
| Citric acid | 1.0 wt % |
| Vitamin B12 | 0.2 wt % |

The above-mixed composition (1 tablet; 380 mg) was tableted, thereby producing tablets.

INDUSTRIAL APPLICABILITY

The present invention can provide a prophylactic or improving/therapeutic agent for chronic fatigue syndrome, idiopathic chronic fatigue, and fibromyalgia, comprising a processed wasabi product as an active ingredient, a food or a beverage, a drug, or a cosmetic, and a drug for preventing or improving/treating diseases relating to chronic fatigue syndrome, idiopathic chronic fatigue, and fibromyalgia, containing the agent, and a method for using them.

The invention claimed is:
1. A method for treating chronic fatigue syndrome, idiopathic chronic fatigue, and fibromyalgia, comprising administering a composition comprising an effective amount of a processed wasabi product, which contains a ω-methylsulfinylalkyl isothiocyanate in an amount ranging from 0.00050 wt % to 0.425 wt % of the total weight of the processed product of a plant of the genus *Wasabia*.
2. The method according to claim 1, wherein the ω-methylsulfinylalkyl isothiocyanate or a physiologically acceptable salt thereof is 6-methylsulfinylhexyl isothiocyanate.

* * * * *